(12) United States Patent
Buffard et al.

(10) Patent No.: US 8,096,989 B2
(45) Date of Patent: Jan. 17, 2012

(54) MOTOR-OPERATED GASTRIC BANDING DEVICE OR GASTRIC RING COMPRISING AT LEAST ONE MISALIGNED RECEIVING ANTENNA FOR POWER SUPPLY, REMOTE CONTROL AND DATA TRANSMISSION BY MEANS OF INDUCTION

(75) Inventors: Laurent Buffard, Lyons (FR); Arnaud Vassor, Annecy (FR)

(73) Assignee: Accessurg (FR)

( * ) Notice: Subject to any disclaimer, the term of this patent is extended or adjusted under 35 U.S.C. 154(b) by 1031 days.

(21) Appl. No.: 11/587,033

(22) PCT Filed: Apr. 21, 2005

(86) PCT No.: PCT/FR2005/000995
§ 371 (c)(1),
(2), (4) Date: Jan. 22, 2008

(87) PCT Pub. No.: WO2005/105001
PCT Pub. Date: Nov. 10, 2005

(65) Prior Publication Data
US 2008/0275478 A1   Nov. 6, 2008

(30) Foreign Application Priority Data

Apr. 21, 2004 (FR) .................................. 04 04223

(51) Int. Cl.
*A61F 2/00* (2006.01)
*A61F 13/00* (2006.01)
*A61B 17/08* (2006.01)

(52) U.S. Cl. ............................ 606/37; 606/151; 606/157
(58) Field of Classification Search .................. 606/151, 606/157, 158, 201, 202; 600/29–31, 37; 607/40, 41, 61, 156; 604/8, 909, 890.1, 891.1; 128/903

See application file for complete search history.

(56) References Cited

U.S. PATENT DOCUMENTS

| | | | | |
|---|---|---|---|---|
| 3,683,389 A | * | 8/1972 | Hollis | 343/788 |
| 5,324,315 A | * | 6/1994 | Grevious | 607/60 |
| 5,388,578 A | * | 2/1995 | Yomtov et al. | 600/375 |
| 5,592,182 A | | 1/1997 | Yao et al. | |
| 5,808,551 A | * | 9/1998 | Yarnall et al. | 340/573.4 |
| 5,938,669 A | * | 8/1999 | Klaiber et al. | 606/157 |
| 6,067,991 A | * | 5/2000 | Forsell | 128/899 |
| 6,141,588 A | * | 10/2000 | Cox et al. | 607/9 |
| 6,248,080 B1 | * | 6/2001 | Miesel et al. | 600/561 |
| 6,305,381 B1 | * | 10/2001 | Weijand et al. | 128/899 |
| 6,449,512 B1 | * | 9/2002 | Boveja | 607/41 |
| 6,450,946 B1 | * | 9/2002 | Forsell | 600/37 |
| 6,460,543 B1 | * | 10/2002 | Forsell | 128/898 |
| 6,461,292 B1 | * | 10/2002 | Forsell | 600/31 |

(Continued)

FOREIGN PATENT DOCUMENTS
EP        0 015 140 A1    9/1980
(Continued)

*Primary Examiner* — Corrine M McDermott
*Assistant Examiner* — Dianne Dornbusch
(74) *Attorney, Agent, or Firm* — DLA Piper LLP (US)

(57) ABSTRACT

A motorized gastric ring or "AGM" including a motor acting on a diameter of the ring and actuated by induction toward an integrated receiving antenna from at least one outer transmitting antenna, wherein the ring includes at least one receiving antenna, the at least one antenna being disoriented relative to a plane extending through the gastric ring, and integrated electronics adapted to substantially optimally use energy received.

12 Claims, 9 Drawing Sheets

U.S. PATENT DOCUMENTS

| | | |
|---|---|---|
| 6,475,136 B1 | 11/2002 | Forsell |
| 6,678,561 B2 * | 1/2004 | Forsell .................. 607/40 |
| 6,680,710 B1 | 1/2004 | Merenda |
| 2002/0042571 A1 * | 4/2002 | Gilboa et al. ............ 600/429 |
| 2002/0044096 A1 | 4/2002 | Chung |
| 2002/0120200 A1 * | 8/2002 | Brockway et al. ......... 600/488 |
| 2002/0138009 A1 * | 9/2002 | Brockway et al. ......... 600/485 |
| 2002/0147388 A1 * | 10/2002 | Mass et al. ............. 600/300 |
| 2002/0177884 A1 * | 11/2002 | Ahn et al. ............. 607/61 |
| 2003/0018365 A1 * | 1/2003 | Loeb .................. 607/40 |
| 2003/0037591 A1 * | 2/2003 | Ashton et al. ............ 73/12.08 |
| 2003/0066536 A1 * | 4/2003 | Forsell ................ 128/899 |
| 2003/0093117 A1 * | 5/2003 | Saadat ................ 606/221 |
| 2003/0100929 A1 * | 5/2003 | Forsell ................ 607/39 |
| 2003/0105385 A1 * | 6/2003 | Forsell ................ 600/29 |
| 2003/0109771 A1 * | 6/2003 | Forsell ................ 600/38 |
| 2003/0125605 A1 * | 7/2003 | Forsell ................ 600/40 |
| 2004/0106967 A1 * | 6/2004 | Von Arx et al. ........... 607/60 |
| 2005/0251181 A1 * | 11/2005 | Bachmann .............. 606/157 |
| 2005/0251182 A1 * | 11/2005 | Bachmann .............. 606/157 |

FOREIGN PATENT DOCUMENTS

| | | |
|---|---|---|
| EP | 0 876 808 A1 | 11/1998 |
| EP | 1 286 477 A1 | 2/2003 |
| FR | 2 756 485 A1 | 6/1998 |
| FR | 2 797 181 A1 | 2/2001 |
| FR | 2 816 828 A1 | 5/2002 |

* cited by examiner

FIG. 10

MOTOR-OPERATED GASTRIC BANDING DEVICE OR GASTRIC RING COMPRISING AT LEAST ONE MISALIGNED RECEIVING ANTENNA FOR POWER SUPPLY, REMOTE CONTROL AND DATA TRANSMISSION BY MEANS OF INDUCTION

RELATED APPLICATION

This is a §371 of International Application No. PCT/FR2005/000995, with an inter-national filing date of Apr. 21, 2005 (WO 2005/105001, published Nov. 10, 2005), which is based on French Patent Application No. 04/04223, filed Apr. 21, 2004.

TECHNICAL FIELD

This disclosure relates to AGMs or motorized gastric rings, that is, of which the diameter of the ring can be regulated by an integrated micromotor.

BACKGROUND

Gastric ring systems of the type comprising an outer chamber and an inner balloon arranged in a physiological liquid contained in the space between the chamber and the balloon are known. A greater or lesser inflation of the balloon increases or reduces the diameter of the gastric ring. The adaptation of the inflation is carried out with the aid of a syringe with which the practicing physician sends a physiological liquid via a reception chamber arranged under an incision in the skin of the patient, and a tube leading to the ring. The disadvantages of such solutions can be imagined: Pain at the level of the permanently arranged chamber, risk of leaks, abuses of manipulations requested on certain occasions by the patients, etc., risk of infection.

Motorized gastric ring apparatus has been developed whose control is carried out by remote control without having recourse to incisions, streams of physiological liquid, reception chamber, tubes, etc.

In particular, FR 2 816 828, EP 0015140 and FR 2 797 181 are known. Those systems essentially comprise a not entirely closed ring intended to be placed around the esophagus, which ring comprises an internal band fixed to one of the ring ends and exiting from the ring by its other end, which band can slide in the ring under the action of a micromotorization (traction system) arranged in a distinct element comprising the motorization, and integrated electronics (electronics for saving energy, processing command signals, supplying the micromotorization, sending command signals to the motorization, managing memories and memory data, updating the data, and other functions of this type).

One skilled in the art will understand that by exerting a traction on the band the ring is tightened around the esophagus and inversely if the traction is loosened. These various apparatus are of great importance.

Figure 1:
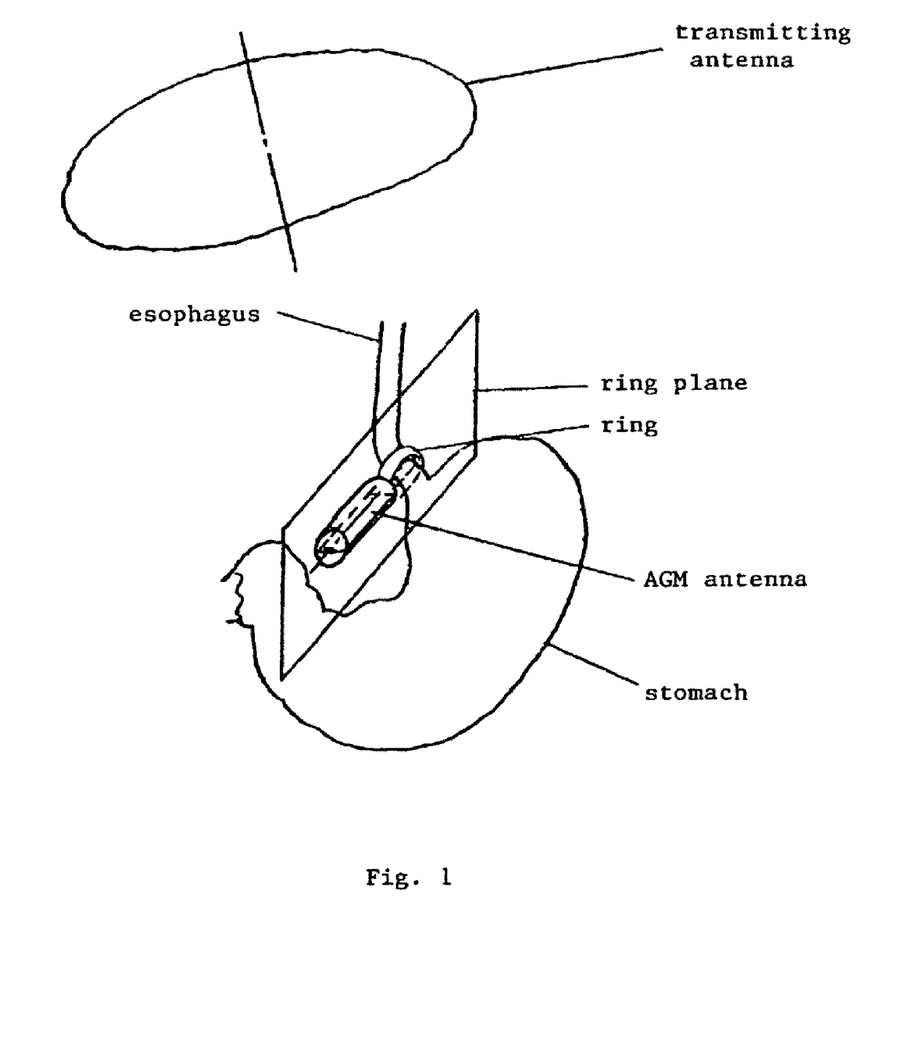
FIG. 1 represents a motorized gastric ring placed around the esophagus with an antenna 90° from the ring plane and with a transmitting antenna.
Figure 4:
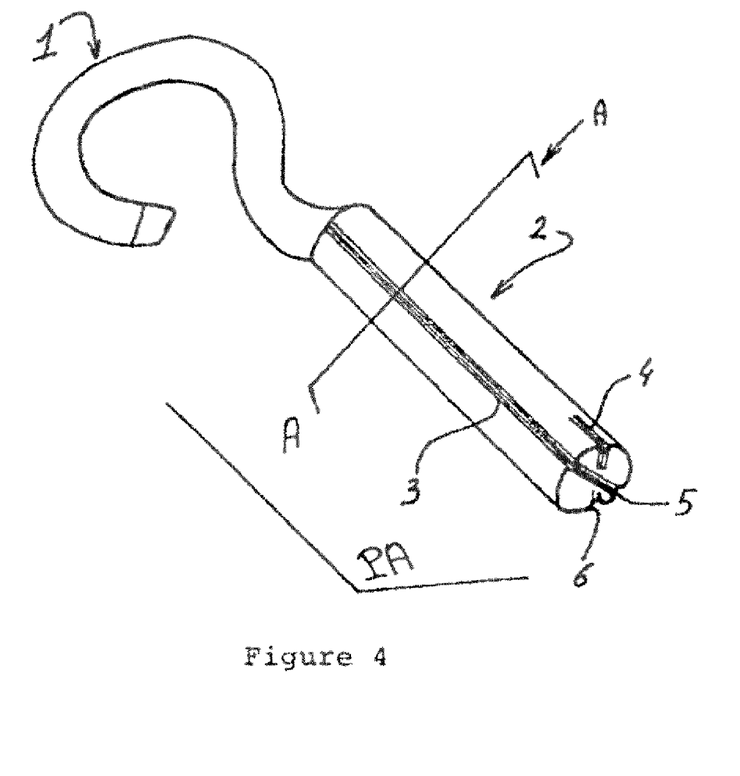
FIG. 4 represents an AGM of the type considered in schematic perspective with its properly named "ring" part 1 and its "integrated motorization-electronic" part or body 2.
Figure 5:
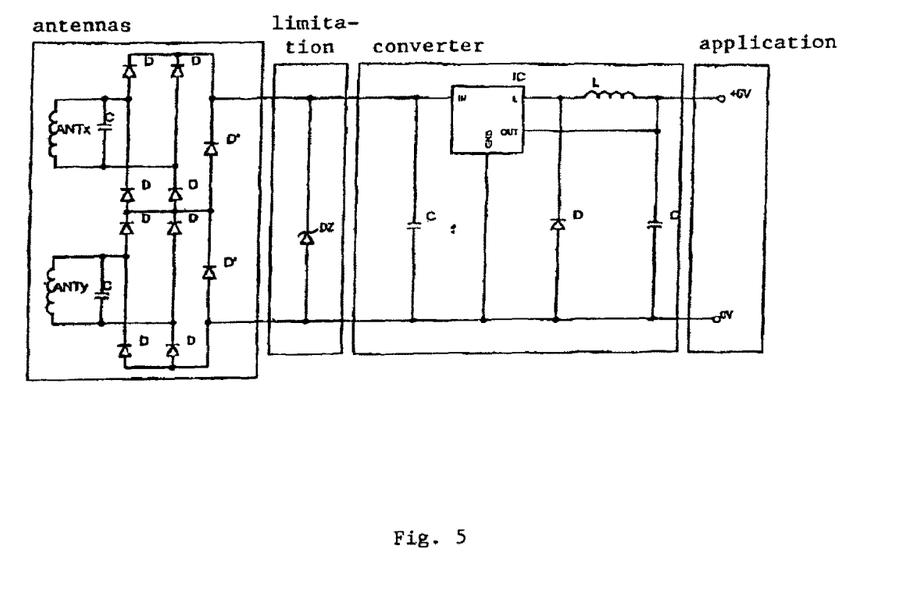
FIG. 5 represents an electric wiring for the coupling of two antennas that can be extrapolated to more than two antennas:
ANT x or y respectively: antenna along the x or y axis;
C capacitor;
D diode;
DZ Zener diode;
L inductance;
IC integrated circuit (allows the voltage to be converted to an appropriate voltage, especially 5V for the AGM application in order to feed the motor and its control circuit)
Figure 6:
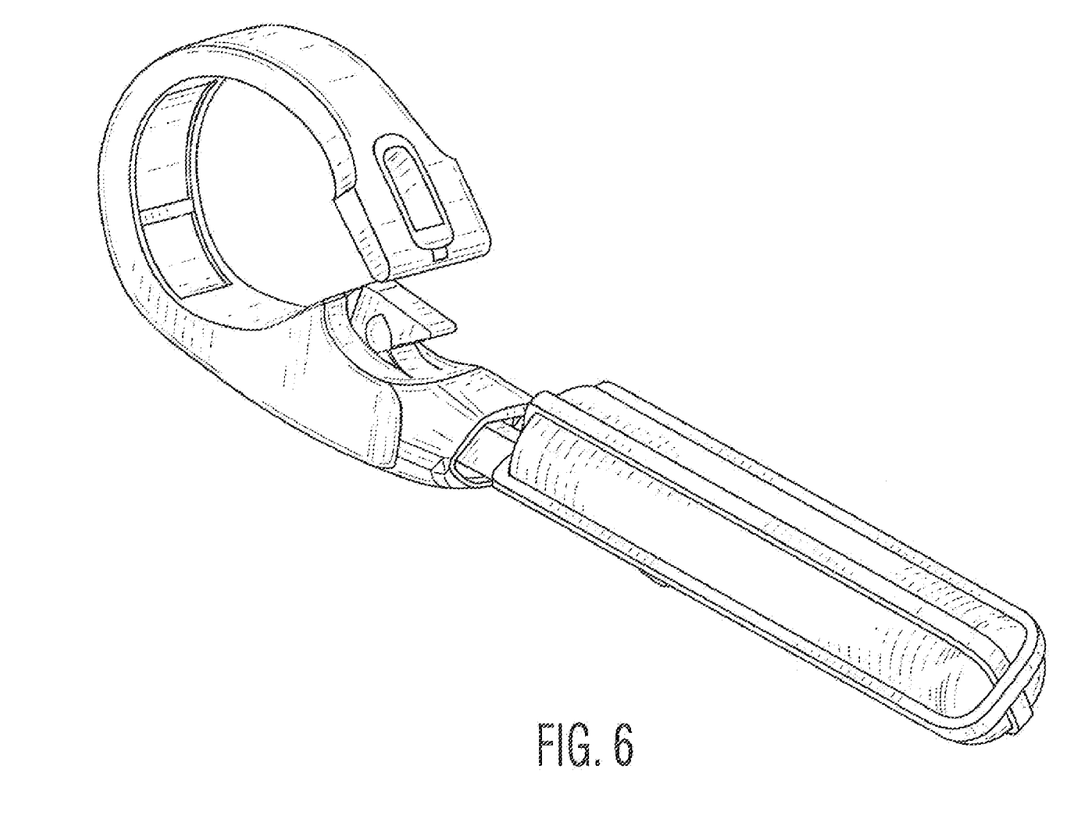
FIG. 6 is a schematic perspective view of an AGM in a two antenna configuration.
Figure 7:
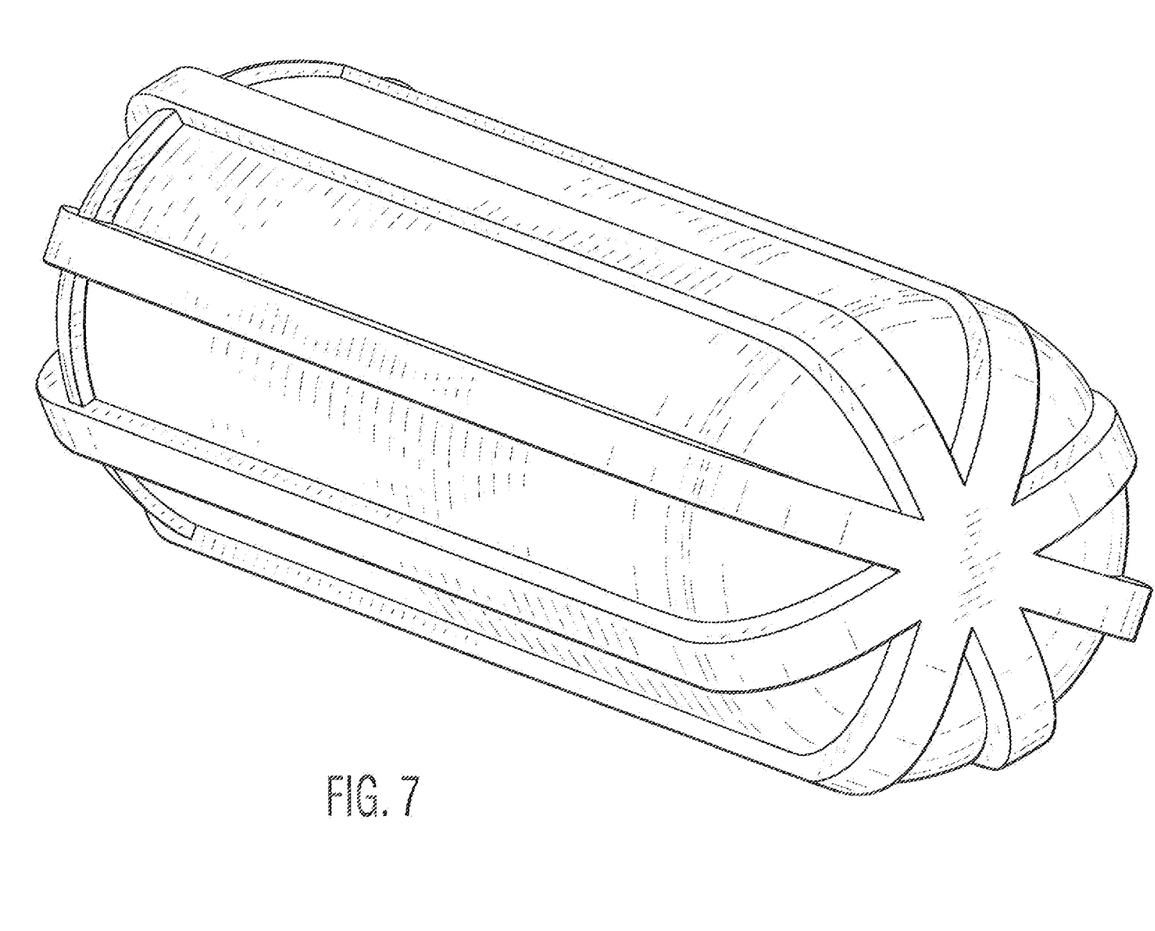
FIG. 7 is a schematic perspective view of a 4 antenna configuration of an AGM.
Figure 8:
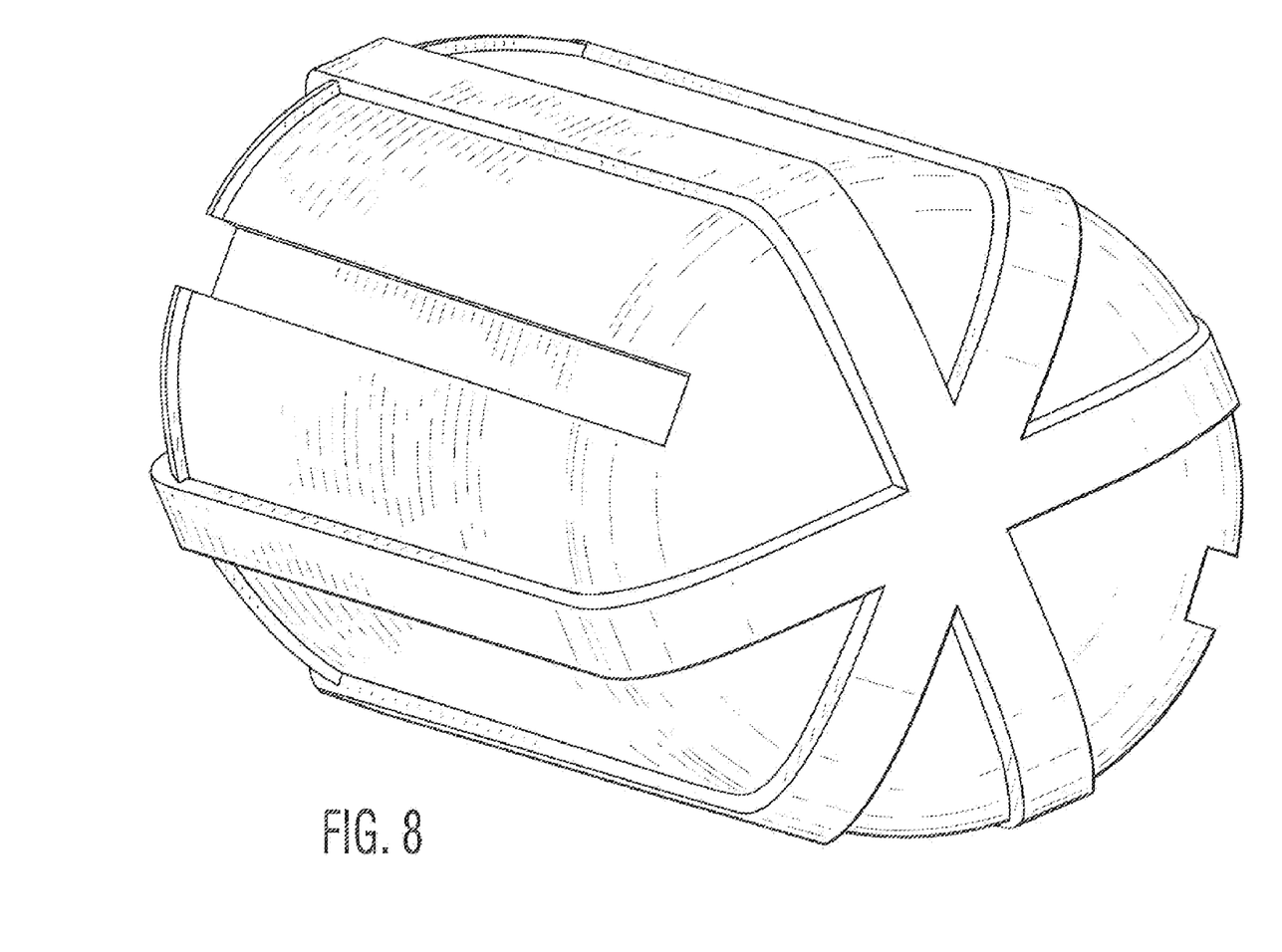
FIG. 8 is a schematic perspective view of 4 antenna configuration with one antenna removed, thereby yielding 3 antennae.

However, a significant problem is posed in the sense that the gastric ring can move after it has been positioned and finally come to rest on certain organs such as the liver or the stomach. It is necessary to define the following elements more precisely to define more accurately the movement which the AGM undergoes:

The AGM is constituted (FIG. 4) of a cylinder 2 containing a motor, electronics and receiving antenna, and the ring 1 placed around the esophagus is located in front of this cylinder. This ring, whose diameter can be increased or reduced, defines a plane whose orientation relative to the transmitting antenna is very important (FIG. 1).

In fact, this orientation determines the quantity of energy received by the ring. Too small a quantity of energy received is expressed at first by a halt in the operation of the motor, then by a halt in the communication with the AGM. The antenna of the AGM versions of the prior art is placed in a standard manner at 90° from the plane formed by the ring.

SUMMARY

This disclosure relates to a motorized gastric ring or "AGM" including a motor acting on a diameter of the ring and actuated by induction toward an integrated receiving antenna from at least one outer transmitting antenna, wherein the ring includes at least one receiving antenna, the at least one antenna being disoriented relative to a plane extending through the gastric ring, and integrated electronics adapted to substantially optimally use energy received.

BRIEF DESCRIPTION OF THE DRAWINGS

Other characteristics and advantages of this disclosure will be better understood from a reading of the following description and by referring to the attached drawings in which.

DETAILED DESCRIPTION

Figure 2:
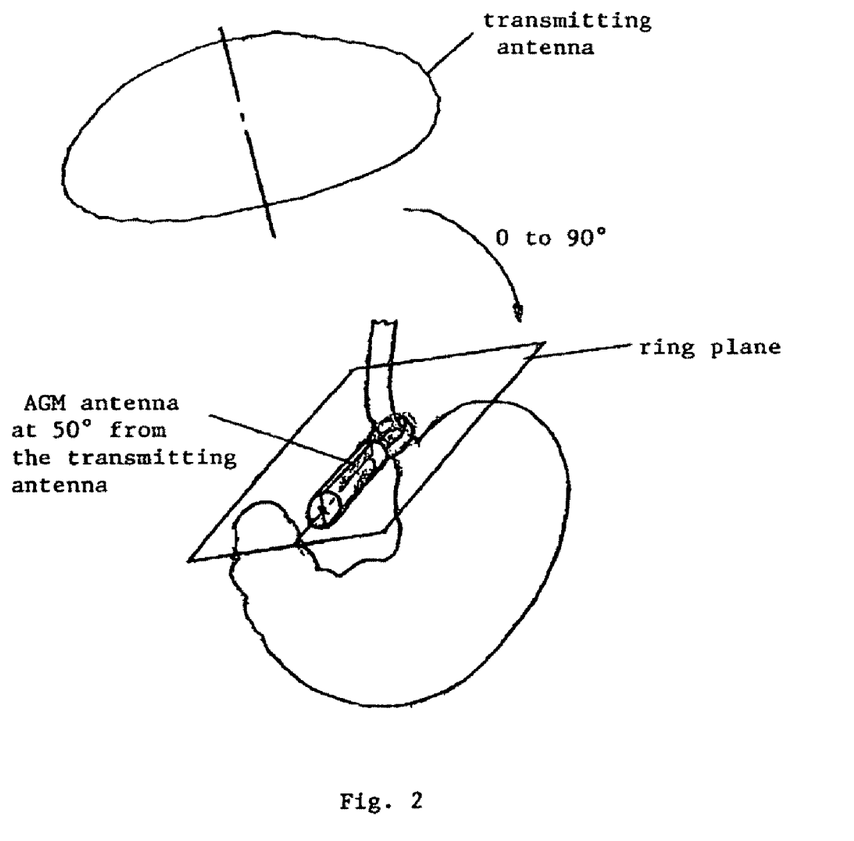
FIG. 2 represents an AGM having undergone a modification of position in the abdomen in general between 0 and 90°, which causes the antenna to pivot all the more relative to the transmitting antenna.

We discovered that the AGM shifts in the patient's body after being implanted, which could not have been foreseen and is, moreover, random. The shifting of the AGM after implanttation results in a rotation that, when it occurs, can be quite considerable in the AGM ring relative to the plane of the outer antenna. This rotation is, in fact, between 0° and 90° relative to the ideal orientation of the ring (ring plane perpendicular to the plane of the transmitting antenna) (FIG. 2).

When these possible rotations are taken into account, the antenna can therefore be at an angle that does not allow sufficient energy to be received to feed the motor and, in certain instances, communication is no longer even possible. This can possibly result in the necessity of repositioning the ring in extreme instances.

It therefore became apparent that it would be helpful to provide a system that ensures, whatever the final position of the motorized gastric ring (AGM), a reception that allows the functioning of the AGM motor at a distance greater than 5 cm.

It is, of course, impossible to sufficiently increase the dimensions of the outer trans-mitting antenna, that must be placed on the abdomen of the patient, nor its power or its trans-mission time (risk, among others, of burns by the antenna upon contact and the risk of the inner heating of the body zone where the apparatus is implanted). Likewise, the choice of the trans-mitting frequency is not free: the frequency must be very far removed from microwave frequencies and must on the contrary correspond to a radiation that is magnetic (without a considerable effect on the patient) and non-electromagnetic.

One solution is to orient the single antenna at an "average" angle, that is to say, intermediate between the position initially adopted (antenna at 90° to the ring) and in antenna in the same plane as the ring. Thus, the antenna is placed at an "average" angle on the order of 45° relative to the ring. This takes into account the possible movements of the motorized ring after it has been positioned and removes the risk of zero reception.

In one aspect, we added at least one second antenna to the first one whether the latter is disoriented as indicated above or whether it is oriented in a standard manner or any intermediate solution. The second antenna (or the supplementary antennas) is/are substantially at a right angle (or at regularly spaced angles in the case of several antennas) relative to the first antenna. This ensures that whatever the angle of rotation of the AGM at least one of the antennas allows a minimum reception of energy that allows the feeding of the AGM motor.

Hence, we provide a motorized gastric ring or "AGM" of the type comprising a motor acting on the diameter of the ring, actuated by induction toward at least one integrated receiving antenna, from an outer transmitting antenna, wherein the ring comprises at least one receiving antenna, at least one of which antennas is disoriented relative to the plane of this gastric ring, that is, the antenna is no longer at a right angle to the plane containing the gastric ring, and integrated electronics adapted in such a manner as to ensure an optimal use of the energy received.

Figure 3:
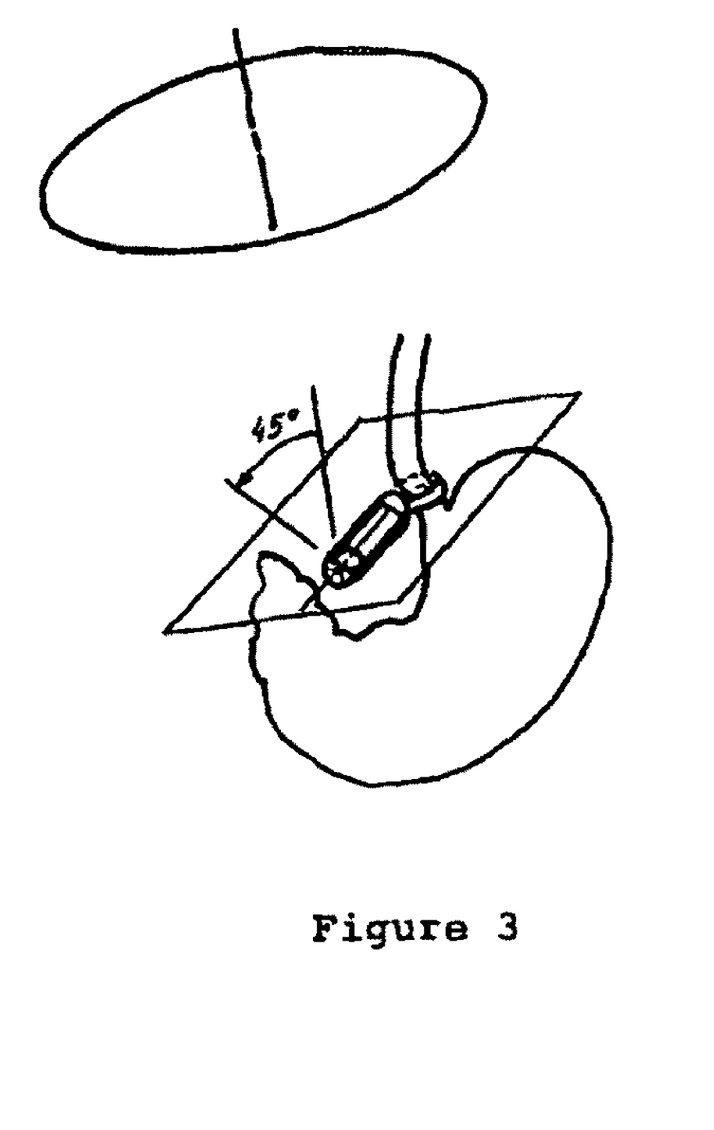
FIG. 3 represents a non-limiting solution in accordance with the invention including a receiving antenna "disoriented" by 45° relative to the ring plane in the configuration of FIG. 2.

The angle that the antenna should have relative to the ring plane should be at least 20° and preferably on the order of 25 to 65° relative to the ring plane. This angle will be trigonometrically positive when viewing the AGM from the end opposed to the ring (FIG. 3).

However, for a disorientation of 45° the power received by the receiving antenna is 70% of the power received with an angle of 0° between the transmitting antenna and the receiving antenna. Such a loss of reception corresponds to diminution of the maximum distance of good functioning of the AGM of 65%.

An advantageous aspect of one disoriented antenna is to arrange two antennas and electronics adapted in such a manner as to allow the best use of the energy received by the antenna that is best oriented to feed the motor. In this configuration the disorientation between the transmitting antenna and the best-placed receiving antenna corresponds to 22.5°.

We therefore also provide a motorized gastric ring characterized in that two antennas are arranged that are angularly offset relative to one another and at least one of which is disoriented and that electronics are arranged that are adapted in such a manner as to allow the best use of the energy received by the antenna that is best oriented to feed the motor.

In this configuration the disorientation between the transmitting antenna and the best-placed receiving antenna corresponds to 22.5° if it is supposed that the transmitting antenna is placed substantially parallel to the abdomen of the carrier of the AGM.

For this difference of orientation the energy received by the best-oriented antenna is 92.4%, which corresponds to a diminution of the maximum distance for good functioning of the AGM of 21.1%.

It will be noted that this type of arrangement meets two significant obstacles: on the one hand, more than one antenna means more space required and greater complexity whereas the available volume and the authorized weight cannot be extended as desired; on the other hand, two antennas or more than two antennas risk having their signals interfere and conflict with each other, up to possibly totally destroying each other. However, our structures do not have that problem.

In one aspect, we provide a motorized gastric ring that comprises at least one antenna with an angular orientation offset by at least 20° relative to the ring plane, preferably at least two antennas with an angular offset for receiving energy intended for the motorization and for the corresponding integrated electronics, energy supplied by induction by at least one outer antenna, which at least two receiving antennas are angularly offset relative to each other, and comprises complementary integrated electronics suitable for using the energy received individually by each antenna.

In another aspect, we provide a motorized gastric ring that comprises at least two angularly offset antennas for receiving energy intended for the motorization and for the corresponding integrated electronics, energy supplied by induction by at least one outer antenna, which at least two receiving antennas are angularly offset relative to each other, and comprises complementary integrated electronics suitable for using the energy received individually by each antenna.

In another aspect, we provide at least two antennas and, in particular, two antennas and provides at least one antenna with an angular orientation offset by at least 20° relative to the ring plane.

The AGM may have two antennas. The two antennas may be angularly offset by 90° from one another. The two antennas may be in planes whose intersection forms the longitudinal axis of the motorization and electronic part of the AGM. The gastric ring advantageously comprises a plurality of antennas offset angularly relative to each other by 45° to 135°.

The AGM may comprise three or four antennas offset angularly in a regular manner. The antennas may be constituted of windings surrounding at least part of the "motorization-electronic integrated" body, preferably in peripheral canals or slots in the surface of the body.

We also provide an AGM of the type described above comprising an electric wiring for the antenna coupling as described in the "process" section above.

We also provide multiple applications of the antenna coupling process as described above for AGMs of all types, especially whose motorization system would be different (pinching/rotation of the two ring branches instead of traction on one band, etc.).

EXAMPLES

Figure 9:
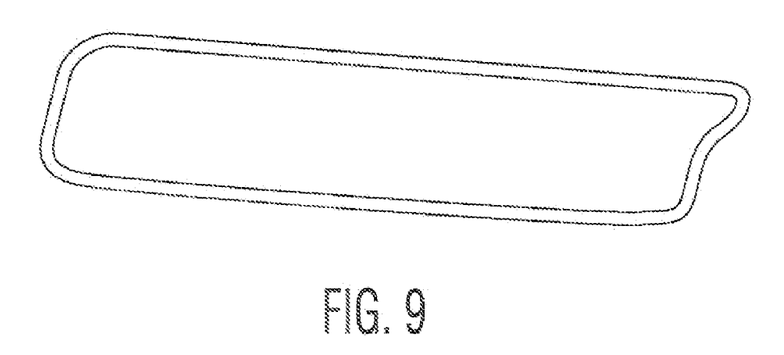
FIG. 9 is a 100 loop antenna.
Figure 10:
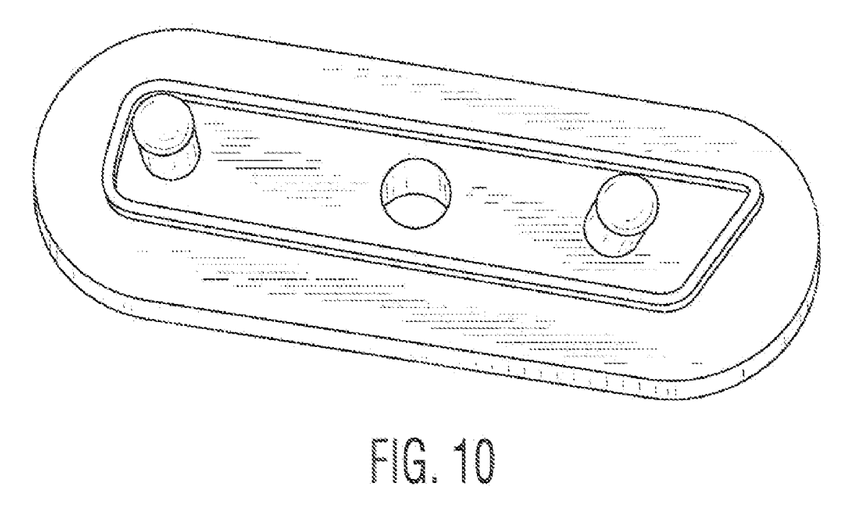
FIG. 10 shows the loop of FIG. 9 on a frame.

A prototype was constructed whose characteristics are as follows:

antenna 3 disoriented by 45° relative to the plane of ring PA, constituted of 100 spirals wound on a frame with a length and a width that has a U-shaped throat (5) with a section of 1.7×2 mm.

antenna 4 at 90° to antenna 3, constituted by 120 spirals wound on a frame 75 mm long and 11 mm wide that has a U-shaped throat (6) with a section of 1.7×2 mm.

By using a transmitting antenna with a diameter of 300 mm fed under 1000 V and 0.3 A, this type of apparatus allows the obtention of the operation of a motor under 40 mA and 5 V from a voltage of 12 V at the output of the voltage limiter at a distance of 15 cm.

This disclosure also covers all embodiments and applications that become directly accessible to one skilled in the art from a reading of this disclosure as defined in the appended claims.

The invention claimed is:

1. A motorized gastric ring or "AGM" comprising:
a body having a longitudinal axis and comprising:
   a) a motor acting on a diameter of the ring and actuated by induction toward an integrated receiving system from at least one outer transmitting antenna, wherein the system comprises at least two receiving antennas each having a longitudinal axis arranged parallel to the longitudinal axis of the body, the at least two receiving antennas being disoriented by an angle of at least 20° relative to a plane of the gastric ring, and
   b) integrated electronics adapted to optimally use energy received by the receiving system from the outer transmitting antenna and for coupling the at least two receiving antennas.

2. The motorized gastric ring according to claim 1, wherein an offset angle of the at least two receiving antennas is trigonometrically positive when viewing the AGM from an end opposed to the ring.

3. The motorized gastric ring according to claim 1, wherein an offset angle of the at least two antennas is between 25 and 65°.

4. The motorized gastric ring according to claim 1, wherein the electronics are adapted to allow use of the energy received by the at least two receiving antennas that is substantially optimally oriented to feed the motor.

5. The motorized gastric ring according to claim 4, wherein disorientation between the transmitting antenna and the at least two receiving antennas is 22.5°.

6. The motorized gastric ring according to claim 4, wherein the at least two receiving antennas are offset angularly by 90° relative to one another.

7. The motorized gastric ring according to claim 4, wherein the at least two receiving antennas are in planes whose intersection forms a longitudinal axis of the motorization and electronic portion of the gastric ring.

8. The motorized gastric ring according to claim 1, wherein the at least two receiving antennas are offset angularly relative to each other by 45° to 135°.

9. The motorized gastric ring according to claim 1, further comprising a third or fourth receiving antenna.

10. The motorized gastric ring according to claim 1, wherein the at least two receiving antennas are constituted of windings surrounding at least part of an integrated motorization-electronic body, in peripheral canals or slots in a surface of the body.

11. The motorized gastric ring according to claim 1, further comprising an electric circuit for coupling the at least two receiving antennas and at least a third and fourth antenna and comprise at least the following elements:
   ANT x or y respectively: antenna along the x or y axis;
   C capacitor;
   D diode;
   DZ Zener diode;
   L inductance;
   IC integrated circuit.

12. The motorized gastric ring according to claim 1, wherein the at least two antennas comprise:
   a first antenna disoriented by 45° relative to the plane of the ring, 100 spirals wound on a frame with a length and a width that has a U-shaped throat with a section of 1.7×2 mm, and
   a second antenna at 90° to the first antenna, constituted of 120 spirals wound on a frame 75 mm long and 11 mm wide that has a U-shaped throat with a section of 1.7×2 mm,
wherein the first and second antennas cooperate with the transmitting antenna, the transmitting antenna having a diameter of 300 mm fed under 1000 V and 0.3 A, and allows obtention of operation of the motor under 40 mA and 5 V from a voltage of 12 V at an output of a voltage limiter at a distance of 15 cm.

* * * * *